United States Patent [19]

Morehouse et al.

[11] Patent Number: 4,782,143

[45] Date of Patent: Nov. 1, 1988

[54] STARCH HYDROLYZATES AND PREPARATION THEREOF

[75] Inventors: Alpha L. Morehouse, Muscatine, Iowa; Pamela A. Sander, Hayfield, Minn.

[73] Assignee: Grain Processing Corporation, Muscatine, Iowa

[21] Appl. No.: 851,969

[22] Filed: Apr. 14, 1986

Related U.S. Application Data

[62] Division of Ser. No. 544,368, Oct. 21, 1983, Pat. No. 4,603,110.

[51] Int. Cl.$^4$ ............................................. C08G 59/00
[52] U.S. Cl. ...................................... 536/102; 435/96; 435/99; 435/205; 435/202; 435/203; 435/204; 127/29; 426/40

[58] Field of Search ................... 536/102; 435/96, 99, 435/205, 202, 203, 204; 127/29; 426/40

[56] References Cited

U.S. PATENT DOCUMENTS 3,792,183  2/1974  Lyall et al. ........................ 426/307
3,962,465  6/1976  Richter et al. ...................... 435/95

Primary Examiner—Joseph L. Schofer
Assistant Examiner—Peter D. Mulcahy
Attorney, Agent, or Firm—Neuman, Williams, Anderson & Olson

[57] ABSTRACT

Starch hydrolyzates having a dextrose equivalent value of not more than about 25 which contain up to about 20% glucose by weight and up to about 40% maltose by weight, with the combination of glucose and maltose not exceeding about 40% by weight of the composition.

1 Claim, No Drawings

STARCH HYDROLYZATES AND PREPARATION THEREOF

This is a division of application Ser. No. 544,368 filed Oct. 21, 1983, now U.S. Pat. No. 4,603,110.

This invention relates to starch hydrolyzate products and to the preparation of such products.

Low dextrose equivalent (D.E.) starch hydrolyzates, below 25 D.E., are widely used in food products as bodying agents, film formers, encapsulating agents, carriers, etc. The known low D.E. starch hydrolyzates usually contain relatively low levels of glucose and maltose, which is highly desirable for many applications. For example, low D.E. starch hydrolyzates disclosed in U.S. Pat. No. 3,663,369 have glucose contents less than about 1% and maltose contents less than about 6% by weight, while the low D.E. starch hydrolyzates disclosed in U.S. Pat. No. 3,849,194 have glucose contents less than about 2.4% and maltose contents less than about 9.7% by weight. However, there are some applications where a higher level of glucose and/or maltose would be desirable to increase the sweetness, browning capacity or some other property not provided by the present products hile retaining most of the inherent advantages of low D.E. starch hydrolyzates. While it is possible to add sugars, such as glucose or sucrose, to the presently known low D.E. starch hydrolyzates, this is undesirable to many food processors under present food labeling regulations. In some instances the food processor would prefer to have a starch hydrolyzate possessing the desired level of glucose and/or maltose as a natural constituent of the hydrolyzate, thereby eliminating the need for separate addition of the sugars and separate listings on the food label.

It is therefore a major object of this invention to provide starch hydrolyzates having a unique and advantageous saccharide composition, including relatively high levels of glucose and/or maltose.

It is another object of this invention to provide novel starch hydrolyzates which provide a very convenient way of incorporating glucose into products in which low dextrose equivalent starch hydrolyzates plus exogenous glucose have been shown to be beneficial, such as in gum confections (U.S. Pat. No. 3,589,909) and pet foods (U.S. Pat. No. 3,617,300).

It is a further object of the invention to provide novel starch hydrolyzates which are useful in applications in which sucrose is added to low dextrose equivalent starch hydrolyzates, such as for breakfast cereal coatings (see U.S. Pat. No. 3,792,183) or certain processes for flavor encapsulation.

It is another object of this invention to provide novel starch hydrolyzates having low dextrose equivalent values and which impart sweetness and browning capacity to food products containing the same.

Another object of the invention is to provide methods for producing starch hydrolyzates having unique and advantageous saccharide compositions.

A further object of the invention is to provide methods for producing novel starch hydrolyzates having relatively low dextrose equivalent values but which contain significant amounts of gluclose and/or maltose which afford desirable attributes thereto.

Another object of the invention is to provide methods for producing novel starch hydrolyzates which are efficient and reliable and which permit handling solids levels which are sufficiently high so as to be commercially feasible.

In addition to the foregoing objects and advantages, the low dextrose equivalent value (D.E.) starch hydrolyzates of the present invention are also of value in food processing to achieve reduction of sucrose levels in foods. Sucrose has been implicated in numerous studies as a contributing factor in certain diseases and health disorders. By use of the starch hydrolyzates of the present invention, food processors can reduce the level of sucrose employed in foods, with the glucose and/or maltose of the starch hydrolyzates providing a sweetening effect.

Another problem which is alleviated by use of the starch hydrolyzates of this invention is the inversion of sucrose during sterilization of acidic beverages. Certain high energy beverages which contain low D.E. hydrolyzates to provide a low osmolality also contain sucrose as a sweetening agent and citric acid for tartness. When these beverages are sterilized, the acid pH causes the sucrose to undergo inversion which results in an undesired increase in osmolality. By formulating the high energy beverage with the starch hydrolyzates of the present invention, the requirement for sucrose is reduced or eliminated and the beverage can be sterilized without an increase in osmolality.

The present invention provides novel starch hydrolyzates having a dextrose equivalent value of not more than about 25 which contain up to about 20% glucose by weight and up to about 40% maltose by weight, with the combination of glucose and maltose not exceeding about 40% by weight of the composition. Preferred starch hydrolyzates contain from about 7 to 20% glucose and from about 4 to 40% maltose with the combination of glucose and maltose not exceeding about 40% by weight of the composition.

The upper limits of glucose and maltose are determined by the upper limit of about 25 D.E. of the new hydrolyzates of this invention. Since any given amount of has only ½ the D.E. value of the same amount of dextrose, it is possible to have nearly twice as much maltose as glucose in the hydrolyzates without exceeding the maximum 25 D.E. value.

The starch hydrolyzates of the invention are produced by treating starch with acid or alpha-amylase to achieve liquefaction followed by treatment with alpha-amylase to achieve saccharification to a relatively low D.E. value, say 5 to 15. The liquefaction and saccharification to provide low D.E. starch hydrolyzates containing relatively small amounts of glucose and maltose can be accomplished by procedures described, for example, in U.S. Pat. Nos. 3,663,369, 3,849,194 and 4,298,400, the disclosures of which are incorporated herein. The resulting low D.E. starch hydrolyzate is then treated with glucoamylase and/or betaamylase to achieve further saccharification and to yield a readily filterable product with a D.E. of not more than 25 and containing a desired amount of glucose and/or maltose. By heating the starch hydrolyzate to temperatures on the order of 100 to 125° C., inactivation of the enzymes is accomplished. The product can then be treated in conventional manner, such as with carbon, if desired, and dried.

According to one presently preferred embodiment of the invention, an aqueous granular starch slurry containing from about 10 to 40% dry solids, more preferably from 20-30% dry solids, is liquefied by heating with acid or alpha-amylase as described in U.S. Pat. No.

3,663,369 or U.S. Pat. No. 4,298,400 to accomplish substantially complete gelatinization of the starch. The pH of the liquefied starch is adjusted to 6-8, preferably pH 6.5-7.5, and treated with bacterial alpha-amylase at a temperature of at least about 95° C., and preferably a temperature in the range of 95° to 100° C., to produce, preferably, a starch hydrolyzate with a D.E. between about 3 and 6, although conversion to higher D.E. values can be accomplished, if desired. The type of alpha-amylase suitable for use is well known to the art and is available commercially under such names as Biocon Canalpha 180, Miles Tenase or Novo BAN. These are bacterial enzymes produced by *Bacillus subtillis*. Another type of bacterial alpha-amylase which may be used is produced by cultures of *Bacillus licheniformis* and is available commercially under the name Novo Termamyl and Miles Taka-Therm. Amylases derived from *Bacillus licheniformis* have a higher saccharifying activity above 95° C. than amylases derived from *Bacillus subtilis* and therefore are more difficult to control to provide a final D.E. of 6 or less.

The level of alpha-amylase suitable for use in the present process is generally in the range of 0.1 to 0.6% based on starch solids when a commercial enzyme product such as the ones listed above is employed. The exact level employed in the high temperature treatment will depend on the D.E. desired, the enzyme activity and the temperature and pH of the reaction. If the D.E. desired in the high temperature treatment step is in the range of 3-4, it is preferred to use a slightly higher temperature than would be required to obtain a 6 D.E. product. Usually for the preparation of hydrolyzates in the 4-6 D.E. range, 0.2 to 0.4% alpha-amylase assaying 3,000 to 4,000 SKB units per gram gives satisfactory results. The reaction time and temperature are closely related; i.e., within the relatively narrow high temperature range at which the alpha-amylase is employed, an increase in temperature shortens the time to attain maximum filterability. Treatment with alpha-amylase for 20 minutes at 95° C. is usually sufficient to provide a filterable hydrolyzate having a D.E. of 6 or less, although the time may be as short as 5 minutes or as long as 40 minutes. In an alternative embodiment when it is desired to produce starch hydrolyzates having higher D.E. values, the hydrolyzate from the high temperature, i.e., above 95° C., treatment can be cooled to a temperature in the range of about 75° to 85° C. and treated further with alpha-amylase to increase the D.E. value to say 10 to 15.

After treatment with alpha-amylase, the starch hydrolyzate is treated with a saccharifying enzyme, such as malt amylase, to increase the maltose content or glucoamylase to increase the glucose content. The further treatment with the saccharifying enzyme is conducted by mixing the starch hydrolyzate with malt amylase or glucoamylase as follows:

1. For malt amylase the enzyme and starch hydrolyzate are mixed at a pH of 4.5 to 6.5, preferably 5 to 6, and a temperature in the range of 40° C. to 60° C., preferably 50° C. to 60° C.

2. For glucoamylase the enzyme and starch hydrolyzate are mixed at a pH of 4.0 to 5.0, preferably 4.2 to 4.6, and at a temperature of 40° C. to 60° C., preferably 50° C. to 60° C.

The period of treatment depends on the amount of glucose and maltose desired in the final product and will generally range from 10 to 90 minutes. For example, to produce a product having a glucose content of 20%, treatment with glucoamylase is conducted for 60 minutes. Likewise, to prepare a product having a maltose content of 25%, treatment with the malt amylase is conducted for 60 minutes. Inactivation of the saccharifying enzyme is achieved by heating to a temperature on the order of 100°-125° C. In addition to malt amylase or glucoamylase, other saccharifying enzymes, such as fungamyl and beta-amylase from soy or wheat can be used.

The starch hydrolyzates of this invention can be derived from all varieties of starch or amylaceous materials, including waxy and non-waxy starches such as potato, milo, wheat, sweet potato, oats, rice, tapioca, corn and the like.

The following examples illustrate the invention and the advantages thereof. In the following examples and throughout this application, $DP_1$ means glucose and $DP_2$ means maltose.

EXAMPLE 1

A starch hydrolyzate was prepared by acid liquefaction of a 30% slurry of corn starch with hydrochloric acid in a commercial jet cooker, followed by neutralization with soda ash to pH 6.8 and addition of bacterial alpha-amylase at a temperature in the range of 95°-99° C. After holding at this temperature for 5 minutes, the starch hydrolyzate was cooled to approximately 80° C. and treated with additional alpha-amylase to provide a starch hydrolyzate having a D.E. of 9.5.

The starch hydrolyzate was then treated with 0.2% glucoamylase (on dry solids; Diazyme L-100) at 60° C. and pH 4.5 for time periods shown below. Samples were taken at intervals and heated to 95° C. to inactivate the enzyme. The composition of the starch hydrolyzate before treatment with glucoamylase, hydrolyzates of the invention and two commercially available starch hydrolyzates are shown in the following table.

| Time at 60° C. | DE | 1 | 2 | 3 | 4 | 5 | 6 | 7 | 8 | 9 | 10 | Above | Ratio: DE ÷ Sum of $DP_1 + DP_2$ |
|---|---|---|---|---|---|---|---|---|---|---|---|---|---|
| Starting 0 minutes | 9.5 | 1.4 | 1.1 | 1.9 | 1.3 | 1.2 | 2.1 | 2.4 | 1.3 | 0.6 | 0.3 | 86.3 | 3.8 |
| 30 minutes | 17.4 | 8.3 | 1.4 | 2.5 | 1.4 | 1.6 | 1.6 | 1.2 | 0.9 | 0.5 | 0.3 | 80.3 | 1.8 |
| 45 minutes | 21.1 | 11.9 | 1.7 | 2.9 | 1.5 | 1.6 | 1.4 | 1.0 | 0.8 | 0.5 | 0.3 | 76.5 | 1.6 |
| 60 minutes | 27.7 | 18.6 | 2.1 | 3.4 | 1.5 | 1.5 | 1.4 | 0.8 | 0.6 | 0.4 | 0.2 | 70.0 | 1.3 |
| MALTRIN M-150* | 15 | 0.7 | 4.5 | 6.6 | 5.3 | 4.4 | 8.6 | 9.8 | 4.9 | 2.9 | 0.3 | 52.0 | 2.9 |
| MALTRIN M-200* | 20 | 2.3 | 7.9 | 9.6 | 6.2 | 5.5 | 12.7 | 9.8 | 2.5 | 0.2 | 0.1 | 43.2 | 2.0 |

*Commercial acid and/or enzyme hydrolyzed corn starch having D.E. values of about 15 and 20, respectively.

The results show that treatment with glucoamylase produced a 6-12 fold increase in glucose with only a 2-3 fold increase in D.E.; thus the definitive ratio is less than 2, with the definitive ratio being the value obtained by dividing the dextrose equivalent value by the sum of the $DP_1$ and $DP_2$ values.

EXAMPLE 2

This example describes the preparation of a starch hydrolyzate with a D.E. of 16.7 and a glucose content of 12.5%. A 4.7 D.E. starch hydrolyzate was prepared by acid liquefaction of a 30% slurry of corn starch with hydrochloric acid in a commercial jet cooker, followed by adjusting the pH to 6.8 and addition of bacterial alpha-amylase at a temperature in the range of 95° C. to 99° C. The material was then held for 20 minutes at 95° C. to 99° C. after which the pH was adjusted to 4.4 before jet cooking to inactivate the alpha-amylase.

A sample of the above hydrolyzate was adjusted to 26% dry solids. The sample was treated at pH 4.4 and 60° C. with 0.2% glucoamylase, on a dry basis, (Diazyme L-100) for 20 minutes. The sample was then heated to 100° C. to inactivate the enzyme, carbon treated and spray dried. The carbohydrate profile of the starch hydrolyzate before treatment with glucoamylase (Sample 1) and the product obtained after glucoamylase treatment (Sample 2) are as outlined below and show that a maltodextrin high in glucose but low in $DP_2$–$DP_{10}$ can be produced by this procedure:

| Sample | DE | DP1 | 2 | 3 | 4 | 5 | 6 | 7 | 8 | 9 | 10 | Above | Ratio: DE ÷ Sum of $DP_1 + DP_2$ |
|---|---|---|---|---|---|---|---|---|---|---|---|---|---|
| 1 | 4.6 | 0.2 | 0.6 | 1.0 | 0.9 | 0.7 | 1.1 | 1.4 | 0.9 | 0.6 | 0.3 | 92.3 | 5.7 |
| 2 | 16.7 | 12.5 | 0.9 | 2.3 | 1.5 | 1.6 | 1.4 | 1.1 | 0.0 | 0.6 | 0.3 | 77.0 | 1.2 |

Sample No. 1 was bland while Sample No. 2 was distinctly sweet.

EXAMPLE 3

The preparation of unique starch hydrolyzates containing maltose or maltose and glucose is shown in this example. Solutions containing 300 grams of a 4.7 D.E. starch hydrolyzate prepared as in Example 2 were treated at pH 4.8 and 60° C. with malt amylase (Wallerstein PF) or malt amylase plus glucoamylase (Diazyme L-100) for periods shown in the following table. After conversion, the samples were heated to a temperature of 100° C. to inactivate the enzyme(s) and the hydrolyzates recovered. A summary of the treatments and composition of the products is given in the following table.

| Sample | Enzyme | Time at 60° C. (minutes) | DE | $DP_1$ | $DP_2$ | Ratio: DE ÷ Sum of $DP_1 + DP_2$ |
|---|---|---|---|---|---|---|
| 1 | 0.13% Glucoamylase + 0.03% Malt Amylase | 10 | 10.7 | 4.0 | 4.0 | 1.3 |
| 2 | 0.13% Glucoamylase + 0.03% Malt Amylase | 20 | 14.6 | 7.6 | 8.1 | 0.9 |
| 3 | 0.13% Glucoamylase + 0.03% Malt Amylase | 30 | 18.6 | 10.2 | 10.7 | 0.9 |
| 4 | 0.03% Malt Amylase | 10 | 6.4 | 0.3 | 4.2 | 1.4 |
| 5 | 0.03% Malt Amylase | 20 | 8.9 | 0.5 | 8.0 | 1.0 |
| 6 | 0.03% Malt Amylase | 30 | 9.7 | 0.5 | 10.9 | 0.9 |

These samples had clean, sweet flavors and were suitable for forming flavored drink products.

EXAMPLE 4

Starch hydrolyzates with dextrose equivalent values less than 25 but containing up to about 30% maltose were prepared as follows:

A 30% dry solids solution of a 4.7 D.E. starch hydrolyzate prepared as in Example 2 was converted at pH 4.5 and 60° C. with 0.1% malt amylase to yield the following starch hydrolyzates:

| | Time at 60° C. (minutes) | DE | % $DP_2$ | Ratio: DE ÷ Sum of $DP_1 + DP_2$ |
|---|---|---|---|---|
| Starch Hydrolyzate No. 1 | 45 | 20.3 | 25.1 | 0.8 |
| Starch Hydrolyzate No. 2 | 55 | 21.6 | 26.7 | 0.8 |
| Starch Hydrolyzate No. 3 | 85 | 24.3 | 30.7 | 0.8 |

The enzyme activity was terminated by heating the samples to 100° C. These samples of unique high maltose starch hydrolyzates were carbon treated, filtered and freeze dried. The flavor of the products was bland and very sweet.

EXAMPLE 5

The following example illustrates the advantage a product of the present invention has over a maltodextrin of the same D.E. and dextrose content prepared by addition of exogenous dextrose.

Aqueous thirty percent solutions of two starch hydrolyzates were prepared as follows:

1. Sample No. 1 was prepared by further treating a 4.7 D.E. starch hydrolyzate with glucoamylase according to the present invention. It had a final D.E. of 16.7 and contained 12.5% glucose.

2. Sample No. 2 was prepared by adding crystalline glucose to a 4.7 D.E. starch hydrolyzate. It had a D.E. of 17.8 and 14.2% glucose.

Aliquots of both solutions were allowed to stand at room temperature. Sample No. 2 became opaque in 4 hours while Sample No. 1 remained clear for 20 hours. Viscosity (RV Brookfield) measurements of aliquots of these samples after 7 days in a refrigerator showed that Sample No. 1 had a lower viscosity (64 centipoises, spindle 2, speed 100) than Sample No. 2 (400 centipoises, spindle 4, speed 100). These results show the advantages of clarity and low viscosity gained by use of the present invention compared to addition of dextrose to maltodextrin.

EXAMPLE 6

Further illustration of the advantage of the present invention over addition of exogenous dextrose is illustrated by the following comparison:

1. Sample No. 1 was a 20.8 D.E. starch hydrolyzate prepared according to the present invention. This sample contained 12.6% glucose.

2. Sample No. 2 was a 23.5 D.E. starch hydrolyzate prepared by combining a conventional maltodextrin (made without the use of a saccharifying enzyme) and crystalline glucose to raise the total glucose level to 12%.

Solutions of the two samples adjusted to 30% dry solids were stored for two weeks in a refrigerator. At the end of this time Sample No. 1 had a slight haze, while Sample No. 2 was opaque.

EXAMPLE 7

Three 3-liter samples of acid-liquefied, non-waxy corn starch were obtained from a commercial starch cooker. The liquefied starch contained 25% solids, had a pH of 7.0 and a D.E. of 5. The samples were then treated as follows:

(1) No alpha-amylase added, held 10 minutes at 80° C.;

(2) 0.2% alpha-amylase added (Canalpha 360), held 10 minutes at 80° C.; and (3) 0.2% alpha-amylase (Canalpha 360) added, held 10 minutes at 96° C.

All samples were then adjusted to pH 4.5, cooled to 60° C. and treated with 0.2% glucoamylase (Diazyme L-100) at 60° C. for the length of time shown below. Acceptable filtration rates were obtained for the final hydrolyzates only after treatment with alpha-amylase at the high temperature (96° C.).

| Preparation of Sample | Length of Glucoamylase Treatment (min.) | DE | Filtration Rate (ml/minute)** |
|---|---|---|---|
| Acid Hydrolyzate* | 0 | 5 | Would not filter |
| Treatment + 10' at 80° C. | 20 | 10.1 | " |
| | 40 | 15.2 | " |
| Acid Hydrolyzate + 10' Alpha-Amylase Treatment at 80° C. | 0 | 10.5 | 40 |
| | 20 | 14.1 | 40 |
| | 40 | 17.3 | 40 |
| Acid Hydrolyzate + 10' Alpha-Amylase Treatment at 96° C. | 0 | 6.8 | 89 |
| | 20 | 14.7 | 140 |
| | 40 | 16.1 | 140 |

*Prior to glucoamylase saccharification at 60° C.
**Filtration Test for Low D.E. Hydrolyzates - A 9 centimeter, jacketed, filtering funnel heated with circulating water at 80° C. was equipped with #1 Whatman filter paper and attached to an aspirator. Two grams of filteraid (Celatom) were added to 200 milliliters of crude hydrolyzate at 75-77° C. and poured into the funnel. A stop watch was used to measure the time to filter the entire sample or the volume filtered in 5 minutes. The filtration time was used to calculate the filtration rate in milliliters per minute.

The saccharide profiles of the novel starch hydrolyzates of this invention are unlike those of previously known low D.E. starch hydrolyzates. In previously known low D.E. starch hydrolyzates the ratio (definitive ratio) of the dextrose equivalent value divided by the sum of the $DP_1$ and $DP_2$ content is usually greater than about 2, whereas for the compositions of this invention the ratio is less than 2. The following table provides a comparison of typical prior art low D.E. starch hydrolyzates with those of the present invention.

| | Saccharide Composition | | | Ratio: DE ÷ Sum of $DP_1 + DP_2$ |
|---|---|---|---|---|
| Sample | DE | $DP_1$ | $DP_2$ | |
| A. Known low D.E. starch hydrolyzates | | | | |
| MALTRIN M-100[1] | 10 | 0.5 | 2.7 | |
| | | 0.7 | 2.8 | 2.8 |
| | | 0.9 | 2.9 | |
| | | 0.6 | 2.4 | |
| MALTRIN M-150[2] | 15 | 0.9 | 3.9 | 2.8 |
| MALTRIN M-200[3] | 20 | 0.7 | 4.5 | |
| | | 2.2 | 7.2 | 2.2 |
| | | 2.3 | 7.9 | |
| MALTRIN M-040[4] | 4.7 | 0.2 | 0.6 | 5.0 |
| Lo-Dex 10[5] | 12.9 | 1.5 | 4.3 | 2.2 |
| Lo-Dex 15[6] | 19.7 | 5.5 | 3.8 | 2.1 |
| B. Starch Hydrolyzates of the present invention | | | | |
| Starch Hydrolyzate A | 8.4 | 4.4 | 0.7 | 1.7 |
| Starch Hydrolyzate B | 11.4 | 8.3 | 1.6 | 1.2 |
| Starch Hydrolyzate C | 17.4 | 13.5 | 1.8 | 1.1 |
| Starch Hydrolyzate D | 23.2 | 17.9 | 1.2 | 1.2 |
| Starch Hydrolyzate E | 6.4 | 0.3 | 4.2 | 1.4 |
| Starch Hydrolyzate F | 9.7 | 0.5 | 10.9 | 0.9 |
| Starch Hydrolyzate G | 20.3 | 0.3 | 25.1 | 0.8 |
| Starch Hydrolyzate H | 24.3 | 0.6 | 30.7 | 0.8 |

Footnotes:
[1] Acid and/or enzyme hydrolyzed corn starch
[2] Acid and/or enzyme hydrolyzed corn starch
[3] Acid and/or enzyme hydrolyzed corn starch
[4] Acid and/or enzyme hydrolyzed corn starch
[5] Acid and/or enzyme hydrolyzed waxy corn starch
[6] Acid and/or enzyme hydrolyzed waxy corn starch The novel starch hydrolyzates have wide applicability and numerous advantages. They can be advantageously used in applications where it is desired to realize the effect of glucose or maltose such as in foods where some sweetness or ability to brown is desired. The new starch hydrolyzates provide quick energy in combination with other desirable qualities of low D.E. starch hydrolyzates. The new starch hydrolyzates can be used to gain body, film-forming, evaporation or low osmolality attributes. The use of these hydrolyzates is particularly convenient and they exhibit improved clarity and filterability over known low D.E. starch hydrolyzates to which extraneous amounts of glucose or maltose are added.

Those modifications and equivalents which fall within the spirit of the invention are to be considered a part thereof.

What is claimed is:

1. A sweetness-imparting starch hydrolyzate having a dextrose equivalent value not above 20 and containing a sweetness-imparting amount of a saccharide component selected from the group consisting of glucose, maltose and combinations thereof, with the total amount of the said saccharide component not exceeding 40% by weight, said starch hydrolyzate having a definitive ratio of not more than 2, said definitive ratio being the quotient obtained by dividing the dextrose equivalent value by the sum of the percentages of glucose and maltose contents, said starch hydrolyzate being prepared by a process which comprises treating an aqueous slurry of starch at a temperature above the gelatinization point with acid or enzyme to liquefy the starch and provide a dispersion substantially free of residual starch granules with a measurable dextrose equivalent not substantially above 3, then treating said dispersion with bacterial alpha-amylase at a temperature of at least about 95° C. to produce a hydrolyzate with a dextrose equivalent not substantially above 6, and then treating the hydrolyzate with a glycogenic or maltogenic saccharifying enzyme to increase the glucose and/or maltose content and to provide a hydrolyzate having a dextrose equivalent value of not more than 20, heating to inactivate the enzymes and recovering the resulting hydrolyzate, and treating the recovered hydrolyzate with carbon and then filtering the treated hydrolyzate.

* * * * *